United States Patent [19]

Nicolaou et al.

[11] Patent Number: 4,977,286

[45] Date of Patent: Dec. 11, 1990

[54] GLYCOLIPIDS

[75] Inventors: Kyriacos C. Nicolaou, Havertown; Thomas J. Caulfield, Philadelphia, both of Pa.

[73] Assignee: Trustees of the University of Pennsylvania, Philadelphia, Pa.

[21] Appl. No.: 242,723

[22] Filed: Sep. 9, 1988

[51] Int. Cl.$^5$ .................... C07C 117/00; C07F 7/18; C07F 117/06

[52] U.S. Cl. ........................................ 552/4; 548/225; 424/85.8; 514/8

[58] Field of Search ............................................ 552/4

[56] References Cited

U.S. PATENT DOCUMENTS

| | | | |
|---|---|---|---|
| 3,944,574 | 3/1976 | Marsden et al. | 552/4 |
| 4,258,199 | 3/1981 | Nicolaou et al. | 549/51 |
| 4,291,166 | 9/1981 | Nicolaou et al. | 549/51 |

OTHER PUBLICATIONS

Ito, Y. et al., *Tetrahedron Lett.*, 1988, 29, 239.
Findeis, M. A. and Whitesides, G. M., *J. Org. Chem.*, 1987, 52, 2838.
Julina, R. et al., Helv. Chimica Acta, 1986, 69, 368.
Roush, W. R. and Adam, M. A., *J. Org. Chem.*, 1985, 50, 3752.
Schmidt, R. R. amd Zimmerman, P., *Tetrahedron Lett.*, 1980, 27, 481.
Hakomori, S., *Scientific American*, 1986, 254, 254, 44.
Schmidt, R. R. and Klager, R., *Anges, Chem. Int. Ed. Engl.*, 1985, 24, 65.
Schmidt, R. R. and Zimmermann, P., *Angew. Chem. Int. Ed. Engl.*, 1986, 25, 725.
Nicolaou, K. C. et al., *J. Am. Chem. Soc.*, 1984, 106, 4189.
Evans, D. A. et al., *J. Am. Chem. Soc.*, 1981, 103, 3099.
Evans, D. A. amd Weber, A. E., *J. Am. Chem. Soc.*, 1987, 109, 7151.
Abel-Magid, A. et al., *J. Am. Chem. Soc.*, 1986, 108, 4595.

*Primary Examiner*—Ronald W. Griffin
*Attorney, Agent, or Firm*—Woodcock Washburn Kurtz Mackiewicz & Norris

[57] ABSTRACT

Novel, optically active azido alcohols are synthesized from N-haloacetyl oxazolidinone and are coupled with protected, activated carbohydrate residues in stereoselective glycosidic fashion to provide glycolipids in substantially pure stereochemical form. In accordance with certain preferred embodiments, the glycosphingolipids globotriaosylceramide, lactosyl ceramide, and galactosyl ceramide are synthesized in substantially pure stereochemical form from alkenyl, C-18 azido alcohols and protected fluoroglycosides and are employed as antigens in the production of antibodies useful, for example, in the treatment of disease.

8 Claims, No Drawings

GLYCOLIPIDS

GOVERNMENT SUPPORT

Portions of this invention were supported by National Institutes of Health Grant GM 36582-02.

BACKGROUND OF THE INVENTION

This invention relates to glycolipids and, more specifically, to glycosphingolipids and the synthesis of glycosphingolipids in substantially pure stereochemical form.

Glycosphingolipids are a class of complex molecules which are embedded in the membranes of cells throughout a wide variety of living organisms. Glycosphingolipids may be generically characterized as glycolipids because they are part lipid and part sugar; glycosphingolipids, however, constitute a special class of glycolipids in that they incorporate into their structures a class of lipids called ceramides, which comprise the lipid sphingosine and a fatty acid tail. Bound to the ceramide portion of the glycosphingolipid molecule is a carbohydrate chain. Variations in structure of both the ceramide and the carbohydrate are possible. In nature, however, certain carbohydrate structures are preferentially linked to certain ceramides. The number of naturally-occurring glycosphingolipids is apparently limited; only about 130 varieties of glycosphingolipids are now known.

That glycosphingolipids are found in all animal cells and in some plant cells has been known for some time. However, it is only recently that the biological function of these molecules has begun to be defined. Because glycosphingolipids are found on the membrane of a cell, it is believed that they help regulate the interactions of the cell with its environment. As a result of their regulatory function, glycosphingolipids are believed to play important roles in a number of serious diseases. It is thought that they may comprise infection receptor sites on the host cell for several kinds of viruses and bacteria.

Recent investigation has determined that brain and nervous tissues are rich in glycosphingolipids. The blood group antigens have also recently been identified as glycosphingolipids. The blood group antigens are found not only in blood but also in many kinds of tissue. For example, they are present in high concentrations on the surface of human epithelial cells, from which more than 90% of all human cancers are derived.

Because glycosphingolipids are present on these cancer prone epithelial cells, they have become objects of great interest by cancer immunologists and others. Immunological approaches to cancer treatment derive from the fact that the body responds to foreign antigens by the production of antibodies which selectively attack those antigens. Bacterial infections, for example, are commonly treated by vaccination with antibodies, similar to those produced by the body's own immune response, which attack antigens on the surface of the bacteria. It has been hypothesized that a cancerous tumor might similarly be treated with antibodies which would attack those antigens associated with the tumor. Many such tumor-associated antigens have been identified as glycosphingolipids; recent immunological studies have shown that many monoclonal antibodies directed against tumor-associated antigens are directed against glycosphingolipids. In addition, a number of studies have established that many types of antigens that are modified or inappropriately expressed in the development of malignant tumors are glycosphingolipids. For example, globotriaosylceramide (hereinafter, $Gb_3$)—one of the most important members of this class of marker molecules—has been highly expressed in most Burkitt lymphoma cell lines, human teratocarcinoma, human embryonal carcinoma, and other types of tumor cells and has been shown to provide the cell surface receptor for verotoxin.

Thus research focusing on glycosphingolipids has been deemed to hold great promise in the treatment of disease, especially cancerous tumors. A considerable amount of work has been done to produce antibodies and reagents that specifically recognize and attack tumor-associated antigens such as glycosphingolipids. In principle, once the antibodies which attack particular tumor-associated antigens are identified, they can be produced in conventional ways and administered to cancer patients such as in a vaccine.

In identifying and growing such antibodies, it is desirable that the particular tumor-associated glycosphingolipid antigens to which the antibodies are directed be available as pure compositions. Commercial formulations of glycosphingolipids are presently available. However, such formulations are generally crude mixtures of a number of different glycosphingolipids and are obtained by involved and difficult extractions from animal and plant material. Synthetic approaches to pure glycosphingolipids in their naturally-occurring forms also have associated drawbacks. Because the glycosphingolipids are complex molecules, a given synthesized glycosphingolipid can comprise many isomeric forms; only one such isomer usually corresponds to the desired naturally-occurring glycosphingolipid, such as may comprise an antigen. Although stereoisomers, or enantiomers, are probably the most similar of all possible types of isomers, the relative reactivities of a naturally-occurring glycosphingolipid antigen and even its enantiomeric form would likely be widely disparate under conditions such as those found in mammals.

Synthetic routes to glycosphingolipids are known in the art, but such routes either provide the desired glycosphingolipid along with isomeric impurities which are removed only with difficulty or entail long experimental procedures which yield enantiomerically pure material only in low overall yield. For example, Schmidt, R. R. and Zimmermann, P., *Angew. Chem. Int. Ed. Engl.*, 1986, 25, 725, teach the synthesis of a glycosphingolipid enantiomer in substantially pure form; the method employed therein involves the boron trifluoride catalyzed coupling of a D-glucosyl trichloroacetimidate with a benzoyl-protected azido derivative of D-erythro-$C_{18}$ sphingosine. This method, however, produces the desired glycosphingolipid product in only about 56% overall yield from these intermediates.

It is therefore desired that short, efficient routes to substantially pure compositions of glycosphingolipids be available to facilitate the research and treatment of cancers and other diseases. Efficient means for synthesizing pure or substantially pure compositions of glycosphingolipids comprising carbohydrate/ceramide combinations not otherwise available from natural sources are also desired.

It is thus an object of this invention to provide synthetic routes to substantially pure glycosphingolipids. A further object is to provide such glycosphingolipids in substantially pure stereochemical form. Yet another object is to effect treatment of cancerous and other diseases by administering to a patient suspected of having the disease an antibody composition effective to result in reduction of the effects of the disease, said antibody composition being prepared using glycosphingolipids synthesized in accordance with this invention.

SUMMARY OF THE INVENTION

This invention provides for improved means for preparing and isolating glycosphingolipids and other glycolipids in substantially pure enantiomeric form. Because the processes employed in accordance with this invention are enantioselective, the removal of isomeric impurities by conventional isolation and purification techniques is diminished or avoided.

The chemical compounds prepared in accordance with this invention have general structure I:

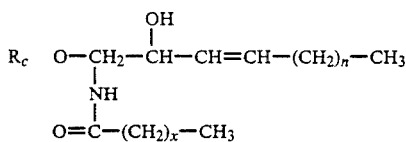

where $R_c$ is a glycosidically-bound carbohydrate residue, n is an integer from 0 to about 25 and x is an integer from 0 to about 30.

It is preferred that n be an integer from about 10 to 14 and that x be an integer from about 14 to 18. It is especially preferred that n be about 12 and that x be about 16. It is believed that virtually any carbohydrate can be employed in the synthetic methods of this invention. Representative carbohydrates from which residues may be derived include glucose, lactose, galactose, glucosamine, sialic acid, N-acetylgalactosamine, and N-acetylglucosamine. Preferred carbohydrates include lactose, galactose, and α-D-galactose-(1-4)-β-D-galactose-(1-4)-β-D-glucose(hereinafter, $p^k$ antigen).

A key element in certain of the synthetic strategies of this invention is the preparation of novel, azido alcohols with general structures II as chemical intermediates.

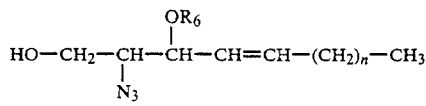

where $R_6$ is hydrogen or a protecting group effective to protect the hydroxyl oxygen during the synthetic schemes and n is an integer from 0 to about 25, preferably about 10 to 14, and more preferably about 12. Such compounds are synthesized from N-haloacetyl oxazolidinones, such as structure III.

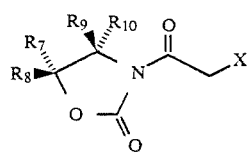

where $R_7$, $R_8$, $R_9$, and $R_{10}$ are the same or different and are hydrogen or a hydrocarbyl moiety having from about 1 to about 7 carbon atoms, and X is a halogen atom. It is preferred that $R_7$, $R_8$, and $R_9$ be hydrogen, that $R_{10}$ be $-CH(CH_3)_2$, and that X be Br. The oxazolidinone fragment is chosen for the directing effect it will have upon later-introduced functionalities.

Compounds having structure III are preferably converted to their enolate form. One means for effecting such conversion is to treat structure III compounds with a base; a preferred base is di-n-butylboron triflate. The enolates thus generated are condensed with alpha, beta-unsaturated aldehydes having structures IV, wherein n is an integer from 0 to about 25, preferably 10 to 4, and more preferably about 12, to form adducts such as structure V, where $R_6$ and Z are H and Y is a halogen. A preferred halogen is bromine.

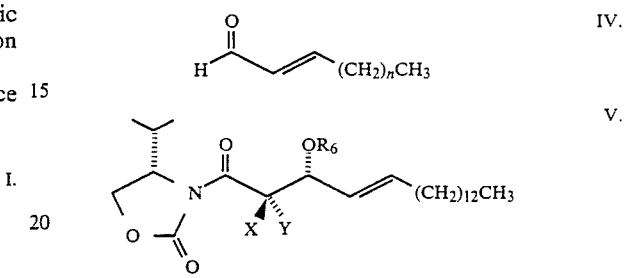

An azide group is then attached with an inversion of stereochemistry to the carbon alpha to the acyclic carbonyl in such adducts. A preferred means of accomplishing this is to treat an adduct having structure V, where $R_6$ and Z are H and Y is Br, with sodium azide in dimethylsulfoxide to yield an azide having structure V where $R_6$ and Y are H and Z is $N_3$.

At this juncture, the free hydroxyl beta to the carbonyl may be protected with a suitable protecting group. An important consideration in the eventual employment of chemical intermediates having structure II in the synthesis of glycolipids is that sensitive functionalities present may prove unstable under reaction conditions such as those employed in this invention. Thus, reactive functionality should be shielded from subsequent reaction conditions through the use of appropriately-chosen protecting groups which may be removed at a later stage of the synthesis. It will be appreciated by those skilled in the art that there are a number of protecting groups from which $R_6$ may be chosen. It is preferred in accordance with embodiments of this invention that $R_6$ be an organosilicon protecting group. It will likewise be appreciated by those skilled in the art that there are a number of organosilicon protecting groups from which $R_6$ may be chosen. However, not all organosilicon protecting groups give good results. For example, in experimenting with tertiarybutyldiphenyl silyl protecting groups, the protecting step proceeded only in low yield after extended reaction periods. It is therefore especially preferred that $R_6$ be $Si(C(CH_3)_3)(CH_3)_2$, which may be attached by reacting the adduct with t-butyldimethylsilyltriflate. Persons of skill in the art will be able to determine other such groups through routine experimentation.

The oxazolidinone fragment is then cleaved, via reduction of the amide functionality, to yield compounds of structure II. One means of effecting such reductive cleavage is to treat the adducts having general structure V with a reducing agent. It is preferred that the reducing agent be a borohydride; it is especially preferred that the reducing agent be lithium borohydride.

An important consideration in the practice of this invention is the stereochemical character of the chemical compounds, such as structure II azido alcohols, which are employed as preferred starting materials and synthetic intermediates. The choice of such compounds depends intimately upon the particular glycolipid product which is ultimately desired since the stereochemical character of such starting materials and chemical intermediates will be transmitted without substantial alteration directly to the products into which they are incorporated. For example, structure II can exist in many isomeric forms, ranging from a single, specific enantiomer to a complex isomer blend. Two particular such enantiomers are the D-erythro and L-erythro isomers of this type of molecular structure, given by perspective diagram in structures VI and VII, respectively.

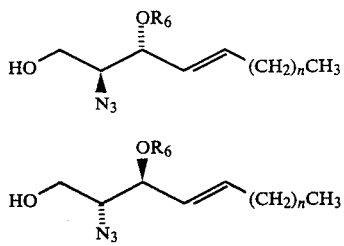

When n is 12, these and other isomeric forms of structure II may be termed sphingosine equivalents because they may be readily converted to sphingosine.

In accordance with this invention, compounds of structure II are stereospecifically coupled to chemically protected, activated carbohydrate residues to yield compounds having structure VIII, where $R_p$ is a carbohydrate residue whose hydroxyl groups are chemically protected from subsequent reaction conditions.

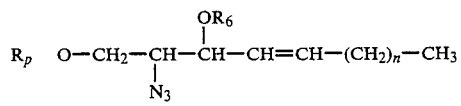

Preferred $R_p$ have structure IX, X, or XI, where Piv is —C(O)C(CH$_3$)$_3$, Ac is —C(O)CH$_3$, and Bz is —C(O)C$_6$H$_5$. Preferred protected, activated carbohydrate residues are given as $R_p$—L, where L is a leaving group. Especially preferred, protected, activated carbohydrate residues are fluoroglycosides given as $R_p$—F, where F is fluorine.

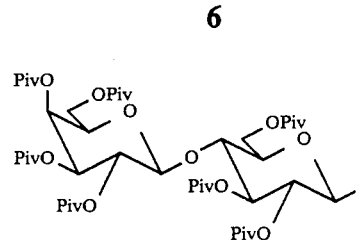

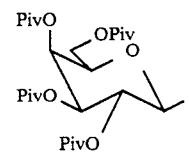

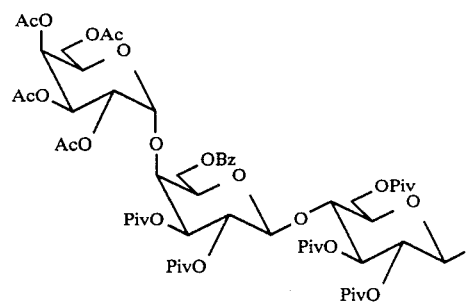

Both the structure II azido alcohol and the protected, activated carbohydrate residue to which it is coupled are chosen so as to be capable of yielding the particular structure I glycolipid product desired. For example, since the naturally-occurring glycosphingolipid Gb$_3$ (structure XII) possess D-erythro stereochemistry, the sphingosine equivalent employed in synthesizing Gb$_3$ is selected to possess the same D-erythro stereochemistry. Thus, in synthesizing Gb$_3$, it is preferred that the sphingosine equivalent having structure VI be coupled with the protected, activated form of p$^k$ antigen having structure XI. XII.

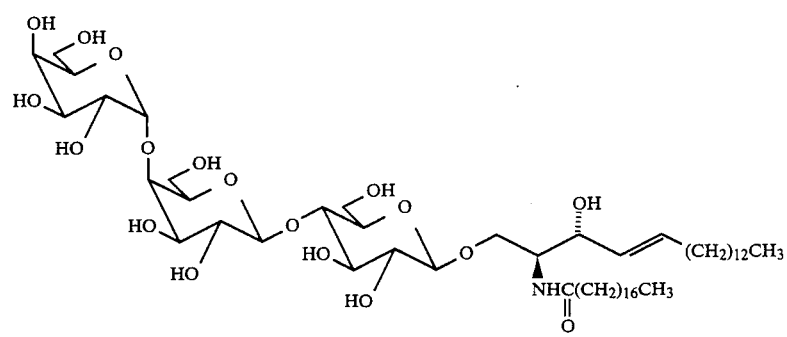

After coupling, the azide group is chemically modified; a representative modification of the azide is its reduction to an amine. A preferred means of effecting this reduction is treatment with a reagent comprising triphenylphosphine and water.

A fatty acid fragment is then appended to the resultant amine function. A preferred means of accomplishing this is to react the amine with an activated fatty acid; preferred activated fatty acids are fatty acid chlorides. Specifically, the reduced form of structure VIII can be reacted with stearoyl chloride to yield structure XIII.

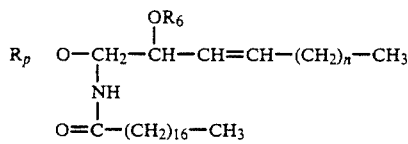

Removal from such molecular structures of any protecting groups employed yields compounds of structure I. For example, the compound of structure XIV where $R_p$ has structure XI may be treated with tetrabutylammonium fluoride and then sodium methoxide to yield the structure I glycosphingolipid Gb$_3$, structure XII. In accordance with this invention, the fatty acid fragment may also be attached to the ceramide moiety prior to glycosidic coupling to a carbohydrate residue, although the presence of an amide at the alpha position has been shown to lower the yield of the coupling step.

Glycolipids thus produced may be advantageously employed in the production of antibodies finding use, for example, in the treatment of disease, especially cancers, and in the detection of diseased cell, especially cancerous cells. Antibodies suitable for use in the methods of the invention may be polyclonal or monoclonal. Polyclonal antibodies may be produced by conventional methods, by injection of an appropriate animal with a glycolipid of the invention as the antigen. Monoclonal antibodies may be produced by methods known in the art for making monoclonal antibodies, starting with a glycolipid of the invention as the antigen.

Antibodies specific for the glycolipid may then be attached to a detectable label by an appropriate method known in the art for the particular label desired. The detectable label may be any ligand which is capable of being detected, directly or indirectly, and thereby indicate that bonding of the antibody to the glycolipid has occurred. The detectable label may be a protein-complexing molecule such as biotin. The detectable label may also be an enzyme capable of causing a color change in a substrate solution. Suitable enzymes are horseradish peroxidase and alkaline phosphatase. The detectable label may also be a radioactive molecule, such as fluorescein, a chemiluminescent molecule, such as luciferin or a light scattering molecule, such as colloidal gold. Suitable detection methods and systems are scintillation counting, autoradiography, fluorescence measurement, colorimetric measurement, light emission or microscopy. The detectable label and method of detecting the detectable label are selected to form a detection system. For example, if the detectable label is fluorescein, a suitable method of detecting the detectable label would be fluorescence measurement.

Antibodies generated with the glycolipids of this invention may be administered directly to patients suspected of having a particular disease as a treatment for that disease. Prior to such administration, said antibodies may also be bound with a molecular structure effective in reducing the affects of any such disease.

The invention is further described in connection with the following examples thereof wherein parts and percents are by weight unless otherwise specified.

EXAMPLE 1

PREPARATION OF A CHEMICAL COMPOUND HAVING STRUCTURE I WHEREIN $R_c$ is LACTOSE, n is 12, and x is 16

A. Preparation and Isolation of Protected Sphingosine Equivalent of Structure II wherein $R_6$ is $Si(C(CH_3)_3)(CH_3)_2$ and n is 12.

To a stirred solution of 11 0 grams (4 S)-3-(bromoacetyl)-4-(isopropyl)-2-oxazolidinone in 150 milliliters of dry diethyl ether at $-78°$ C. was added 8.6 milliliters triethylamine. After about 5 minutes, 11.3 milliliters dibutylboron triflate was added slowly via syringe. After 15 minutes, the reaction mixture was allowed to stir at room temperature for 2 hours. At the end of this time, the reaction mixture was slowly cooled back down to $-78°$ C. and a solution of 6.66 grams E-hexa-dec-2-eneal in 130 milliliters dry diethyl ether was added via cannula. The reaction mixture was stirred at $-78°$ C. for 45 minutes, then at 0° C. for 1.5 hours. At the end of this time, the reaction was diluted with 250 milliliters diethyl ether and poured over 150 milliliters of 1N aqueous NaHSO$_4$. The layers were separated and the organic layer was washed with 150 milliliters 1N aqueous NaHSO$_4$ followed by 150 milliliters brine. The ether layer was concentrated in vacuo and the resulting residue redissolved in 150 milliliter diethyl ether and cooled to 0° C. To this stirred mixture was slowly added 150 milliliters of a 1:1 solution of methanol and 30% aqueous H$_2$O$_2$. After the addition, the reaction mixture was allowed to stir at 0° C. for 1 hour. At the end of this time, the reaction was diluted with 200 milliliters diethyl ether and poured over 200 milliliters saturated aqueous NaHCO$_3$. The layers were separated and the aqueous layer extracted twice with 100 milliliters diethyl ether. The ether layers were combined and washed twice with 150 milliliters saturated aqueous NaHCO$_3$, then once with 150 milliliters of brine. The ether layer was dried (MgSO$_4$) and concentrated. Flash chromatography (silica 15% ethyl acetate in petroleum ether) afforded 10.21 grams of a compound having structure V where $R_6$ and Z are H and Y is Br.

To a stirred solution of this compound (10.21 grams, 20.9 millimoles) in dry dimethylsulfoxide (53 milliliters) was added sodium azide (2.67 grams). Using thin layer chromatography, the reaction was determined to be complete in 2 hours. The reaction was diluted with diethyl ether (300 milliliters), washed with water (3×100 milliliters) and brine (100 milliliters), dried (MgSO$_4$) and concentrated. Flash chromatography (silica, 20% ethyl acetate in petroleum ether) yielded a compound having structure V where $R_6$ and Y are H and Z is N$_3$.

To a stirred solution of this compound (6.81 grams, 15.11 millimoles) in dry tetrahydrofuran (75 milliliters) at 0° C. was added 2,6-lutidine (3.5 milliliters) followed by t-butyldimethylsilyltriflate (5.2 milliliters). After 0.5 hours stirring at 0° C., the reaction mixture was allowed to stir at room temperature for 1.0 hour. The reaction mixture was diluted with ethyl acetate (250 milliliters), washed with water (100 milliliters) and brine (100 milliliters), dried (MgSO$_4$), and concentrated. Flash chromatography (silica, 7% ethyl acetate in petroleum ether) yielded a compound having structure V where $R_6$ is $Si(C(CH_3)_3)(CH_3)_2$, Y is H, and Z is N$_3$.

To a stirred solution of this compound (7.43 grams, 13.15 millimoles) in dry tetrahydrofuran (66 milliliters) was added lithium borohydride (859 milligrams) in portions. The reaction mixture was stirred below 0° C. for 1.5 hours when the ice bath was removed and the reaction stirred at room temperature for 0.5 hours. The reaction was cooled back down to 0° C., diluted with ethyl acetate (100 milliliters) and the excess lithium borohydride quenched by the slow addition of a saturated aqueous NH$_4$Cl solution (100 milliliters). The layers were separated and the aqueous layer was extracted with ethyl acetate (2×100 milliliters). The organic layers were combined, dried (MgSO$_4$) and concentrated. Flash chromatography (silica, 10% ethyl acetate in petroleum ether) yielded as an oil the compound having structure VII where R$_6$ is Si(C(CH$_3$)$_3$)(CH$_3$)$_2$, protected sphingosine equivalent. Rf=0.33 (silica, 2% ether in CH$_2$Cl$_2$); [α]$_D^{22}$= −40.5° (c=4.5, CHCl$_3$): IR (neat) v$_{max}$ 3510 (m), 2940 (s), 2865 (s), 2115 (s), 1210 (s), 1095 (s) cm$^{-1}$; $^1$H NMR (500 MHz, CDCl$_3$) δ 5.65 (dt, J=7.0, 15.4 Hz, 1H, C=C—H), 5.42 (dd, J=6.8, 15.4 Hz, 1H, C=C—H), 4.12 (dd, J=5.6, 6.7 Hz, 1H, CH-OSi), 3.66–3.58 (m, 2H, CH$_2$—OH), 3.36 (m, 1H, CH—N$_3$), 2.52 (bs, 1H, OH), 2.01 (dt, J=7.0, 7.2 Hz, 2H, C=C—CH$_2$), 1.35–1.22 (m, 22H, CH$_2$), 0.91–0.84 (m, 12H, Si$^{tBu}$ $^{CH}$$_2$), 0.06 and 0.01 (singlets, 3H each, SiMe$_2$); $^{13}$C NMR (125 MHz, CDCl$_3$) 134.6, 129.0, 75.0, 67.9, 68.9, 32.2, 9.6, 29.4, 29.3, 28.9, 25.7, 22.6, 17.9, 14.0.

B. Coupling of the Protected Sphingosine Equivalent with a Carbohydrate Fragment and Isolation of the Glycosphingolipid Product.

To a stirred mixture of silver perchlorate (648 milligrams), stannous chloride (0.59 milligrams), flame-activated 4 Angstrom molecular sieves (which had been dried azeotropically with benzene (2×10 milliliters)), and CH$_2$Cl$_2$ (10 milliliters) was added dry 2,6-lutidine (0.15 milliliters). The reaction mixture was cooled down to −28° C. and a solution of protected sphingosine equivalent (549 milligrams, 1.25 millimoles) in CH$_2$Cl$_2$ (6 milliliters) was added via syringe. After 10 minutes a solution of R$_p$F, where R$_p$ has structure IX, (1.4 grams, 1.50 millimoles) in CH$_2$Cl$_2$ (6 milliliters) was added slowly via syringe. The reaction mixture was allowed to stir in the dark while slowly warming to room temperature. After 14 hours, the reaction was diluted with ethyl acetate (50 milliliters) and filtered through a pad of celite. The filtrate was washed with saturated aqueous NaHCO$_3$ (3×30 milliliters) and brine (30 milliliters), dried (MgSO$_4$) and concentrated. Flash chromatography (1%–2% diethyl ether in CH$_2$Cl$_2$) afforded a compound having structure VIII where R$_p$ has structure IX and R$_6$ is Si(C(CH$_3$)$_3$)(CH$_3$)$_2$.

To a stirred solution of this compound (1.15 grams, 0.849 millimoles) in benzene (4 milliliters) at 45° C. was added triphenylphosphine (0.445 grams). After 0.5 hours, water (0.15 milliliters) was added and the reaction continued to stir at 45° C. After 6 hours the reaction was cooled, diluted with ethyl acetate (50 milliliters), washed with saturated aqueous NH$_4$Cl (25 milliliters), dried (MgSO$_4$) and concentrated. Flash chromatography (silica, 25% ethyl acetate in petroleum ether) afforded as a white foam structure XIV, where R$_p$ has structure IX and R$_6$ is Si(C(CH$_3$)$_3$)(CH$_3$)$_2$ Rf=0.24 (20% EtOAc in petroleum ether); [α]D$^{22}$ −6.55° (c=2.58, CHCl$_3$); IR (CCl$_4$ smear) v$_{max}$ 3470 (w), 3395 (w), 2985 (s), 2940 (s), 2860 (s), 1750 (s), 1490 (s), 1285 (s) cm$^{-1}$; $^1$H NMR (500 MHz, CDCl$_3$) δ 5.59 (dt, J=6.6, 15.4 Hz, H,C=C—H), 5.38 (d, J=3.2 Hz, 1H, H-4′), 5.30 (dd, J=7.4, 15.4 Hz, 1H, C=C—H), 5.21 (dd, J=9.6 Hz, 1H, H-3), 5.11 (dd, J=8.1, 10.4 Hz, 1H, H-2′), 4.96 (dd, J=3.3, 10.4 Hz, 1H, H-3′), 4.83 (dd, J=7.9, 9.7 Hz, 1H, H-2), 4.51 (m, 1H, H-6$_a$), 4.50 (d, J=8.0 Hz, H, H-1′), 4.47 (d, J=7.9 Hz, 1H, H-1), 4.20 (dd, J=4.6,12.0 Hz, 1H, H-6$_b$), 4.10 (dd, J=7.4, 11.3 Hz, 1H, H-6$_a$′), 4.01 (dd, J=6.1, 11.3 Hz, 1H, H-6$_b$′), 3.93–3.87 (m, 3H, H-4, H-5′, CH—OSi), 3.71 (dd, J=7.1, 9.4 Hz, 1H, H-a), 3.58 (dd, J=3.6, 9.4 Hz, 1H, H-a′), 3.53 (m, 1H, H-5), 2.74 (m, 1H, CH—N), 2.00 (dt, J=6.6, 7.0 Hz, 2H, C=C—CH$_2$), 1.43–1.07 (m, 85H, CH$_2$), 0.88–0.83 (m, 12H, SiC(CH$_3$)$_3$), CH$_3$), 0.04 and 0.01 (singlets, 3H each, Si(CH$_3$)$_2$); $^{13}$C NMR (125 MHz, CDCl$_3$) δ 177.2, 177.0, 176.8, 176.7, 176.0, 134.0, 130.1, 101.4, 100.0, 75.3, 73.3, 72.2, 71.8, 71.7, 71.4, 68.8, 66.8, 61.3, 56.0.

To a stirred solution of this compound (639 milligrams, 0.487 millimoles) in CH$_2$Cl$_2$ (2.5 milliliters) at 0° C. was added triethylamine (0.10 milliliters) and dimethylaminopyridine (5 milligrams) followed by the slow addition of stearoyl chloride (0.20 milliliters). After 1.5, the reaction was diluted with ethyl acetate (30 milliliters), washed with water milliliters), saturated aqueous NaHCO$_3$ (2×10 milliliters), and brine (10 milliliters), dried (MgSO$_4$) and concentrated. Flash chromatography (silica, 5% diethyl ether in CH$_2$Cl$_2$) gave, as a white foam, structure XIV, where R$_p$ has structure X and R$_6$ is Si(C(CH$_3$)$_3$)(CH$_3$)$_2$. Rf=0.41 (5% ether in CH$_2$Cl$_2$); [α]$_D^{22}$ −7.13 (c=2.16, CHCl$_3$); IR (CCl$_4$ smear) v$_{max}$3460 (w), 2980 (s), 2940 (s), 28970 (s), 1750 (s), 1690(s), 1490 (s), 1285 (s) cm$^{-1}$; $^1$H NMR (500 MHz, CDCl$_3$) δ 5.52 (dt, J=7.1, 15.3 Hz, 1H, C=C—H), 5.40 (d, J=8.8 Hz, H, NH), 5.35 (d, J=3.3 Hz, 1H, H-4′), 5.28 (dd, J=7.6, 15.4 Hz, 1H, C=C—H), 5.18 (dd, J=9.5 Hz, 1H, H-3), 5.07 (dd, J-8.2, 10.3 Hz, 1H, H-2′), 4.92 (dd, J=3.3, 10.5 Hz, 1H, H-3°), 4.78 (dd, J=7.9, 9.5 Hz, 1H, H-2), 4.46 (d, J=8.1 Hz, 1H, H-1′), 4.42 (d, J=7.8 Hz, 1H, H-1), 4.40 (m, 1H, H-6$_a$), 4.20 (dd, J=4.8, 12.1 Hz, 1H, H-6$_b$), 4.09–4.06 (m, 2H, H-6$_a$′, CH-OSi), 4.02 (dd, J=4.1, 9.6 Hz, 1H, H-a), 3.98 (dd, J=6.2, 11.2 Hz, 1H, H-6$_b$′), 3.91 (m, 1H, CH—N), 3.88 (dd, J=6.4 Hz, 1H, H-5′), 3.85 (dd, J=9.5 Hz, 1H, H-4), 3.50 (m, 1H, H-5), 3.41 (dd, J=3.7, 9.6 Hz, 1H, H-a′), 3.04–2.91 (m, 4H, C(O)—CH$_2$, C=C—CH$_2$), 1.50 (m, 2H, C(O)—C—CH$_2$), 1.33–1.03 (m, 113H, CH$_2$ and pivalates), 0.84–0.80 (m, 15H, SiC(CH$_3$)$_3$ and 2×CH$_3$), −0.04 and −0.06 (singlets, 3H each, Si (CH$_3$)$_2$); $^{13}$C NMR (125 MHz, CDCl$_3$) 177.6, 177.5, 177.2, 176.9, 176.8, 176.7, 175.9, 172.3, 133.7, 130.2, 100.9, 99.9, 76.7, 73.5, 73.1, 71.9, 71.6, 71.4, 68.8, 67.9, 66.8, 66.7, 61.8, 61.2, 53.3.

To a solution of this compound (629 milligrams, 0.39 millimoles), in tetrahydrofuran (2.0 milliliters) was added 0.59 milliliters of a 1.0 molar solution of tetrabutylammoniumfluoride in tetrahydrofuran. After 2 hours, the reaction was diluted with ethyl acetate (20 milliliters) and poured over saturated aqueous NH$_4$Cl (20 milliliters). The layers were separated and the aqueous layer extracted with ethyl acetate (20 milliliters). The organic layers were combined, dried (MgSO$_4$) and concentrated. Flash chromatography (silica, 10% diethyl ether in CH$_2$Cl$_2$) gave, as a white foam, structure I, where R$_c$ is R$_p$ and has structure XI, n is 6 and x is 18. Rf=0.31 (10% ether in CH$_2$Cl$_2$); [α]$_D^{22}$ −4.96 (c=5.0, CHCl$_3$); IR (CCl$_4$ smear) v$_{max}$ 3480 (m), 2980 (s), 2940 (s), 2875 (s), 1750 (s), 1690 (s), 1490 (s) cm$^{-1}$; $^1$H NMR (500 MHz, CDCl$_3$) δ 5.82 (d, J=7.9 Hz, 1H, NH), 5.66 (dt, J=7.0, 15.4 Hz, 1H, C=C—H), 5.44 (dd, J=6.9, 15.4 Hz, 1H, C=C—H), 5.40 (d, J=3.1 Hz, 1H, C-4'), 5.23 (dd, J=9.6 Hz, 1H, H-3), 5.14 (dd, J=8.1, 10.5 Hz, 1H, H-2'), 5.01 (dd, J=3.2, 10.2 Hz, 1H, H-3'), 4.81 (dd, J=7.9, 9.3 Hz, 1H, H-2), 4.70 (d, J=12.1 Hz, 1H, H-6$_a$), 4.58 (d, J=8.0 Hz, 1H, H-1'), 4.46 (d, J=7.9 Hz, 1H, H-1), 4.20 (dd, J=4.1, 12.1 Hz, 1H, H-6$_b$), 4.13 (dd, J=7.1, 11.1 Hz, 1H, H-6$_a$'), 4.07–3.90 (m, 5H, H-4,H-5', H-6$_b$', CH—N, CH—OH), 3.61 (dd, J=3.1, 9.8 Hz, 1H, H-a), 3.53 (d, J=9.8 Hz, 1H, H-a'), 3.52 (m, 1H, H-5), 3.04 (d, J=7.3 Hz, 1H, OH), 2.11 (t, J=7.6 Hz, 2H, C(O)—CH$_2$), 2.01 (dt, J=7.0 7.2 Hz, 2H, C=C—CH$_2$), 1.5s (m, 2H, C(O)—C=CH$_2$), 1.47–1.06 (m, 113Hz, CH$_2$ and pivalates), 0.86 (t, J=7.3 Hz, 6H, 2×CH$_3$); $^{13}$C NMR (125 MHz, CDCl$_3$) δ 177.7, 177.3, 177.0, 176.8, 176.7, 176.0, 173.0, 134.1, 128.8, 100.7, 100.0, 73.7, 73.2, 72.7, 71.7, 70.9, 68.7, 66.8, 61.1.

All of this white foam was dissolved in 0.5 milliliters tetrahydrofuran; methanol (1.0 milliliters) was added followed by sodium methoxide (9 milligrams). The reaction was heated to 65° C. After 14 hours, the reaction was diluted with methanol (5 milliliters); Amberlist resin (10 milligrams) was stirred into the reaction until neutral. The resin was filtered off and the filtrate concentrated. Flash chromatography (silica, 60:25:4-CHCl$_3$:methanol:H$_2$O) yielded the lactosyl ceramide having structure I where R$_c$ is lactose, n is 16 and x is 18. R$_f$=0.65 (silica, CHCl$_3$:methanol:water 60:25:4); $[\alpha]_D^{22}$ +0.4° (c=0.4, DMSO); $^1$H NMR (500 MHz, DMSO-d$_6$:D$_2$O, 98:2) δ 7.46 (d, J=9.1 Hz, 1H N—H), 5.52 (dt J=7.5, 15.1 Hz, 1H, C=C—H), 5.34 (dd, J=7.0, 15.1 Hz, 1H, C=C—H), 4.19 (d, J=7.0, 1H, H-1'), 4.15 (d, J=7.7 Hz, 1H, H-1), 3.96 (m, 1H), 3.86 (t, J=7.5 Hz, 1H, CH—O), 3.77–3.71 (m, 2H, H-3', CH—N), 3.60–3.28 (m, 11H, CH—O), 3.31 (s, HDO), 3.03 (dd, J=7.9, 8.0 Hz, 1H, H-2), 2.01 (t, J=7.24 Hz, 2H, CH$_2$—C(O)), 1.92 (m, 2H, C=C—CH$_2$), 1.42 (m, 2H, CH$_2$≧C(O)), 1.38–1.07 (m, 50H, CH$_2$). 0.84 (t, J=6.7 Hz, 6H, 2×CH$_3$).

EXAMPLE 2

PREPARATION OF A CHEMICAL COMPOUND HAVING STRUCTURE I WHEREIN R$_c$ is GALACTOSE, n is 12, and x is 16

The method in Example 1, Section B was followed, except that 0.979 grams sphingosine equivalent in 10 milliliters methylene chloride and 1.73 grams of glycolsyl donor R$_p$F, where R$_p$ has structure XI, in 10 milliliters methylene chloride were added to a flask containing 692 milligrams AgClO$_4$, 633 milligrams SnCl$_2$, 1.2 grams 4.0 Angstrom molecular sieves and 234 microliters 2,6-lutidine in 13.5 milliliters methylene Chloride. A product having structure VIII, where R$_p$ has structure XI and R$_6$ is Si(C(CH$_3$)$_3$)(CH$_3$)$_2$, was isolated by flash chromatography with 5% ethyl acetate in petroleum ether. Rf=0.54 (10% ethyl acetate in petroleum ether); $[\alpha]_D^{24}$=−14.2° (c=0.53, CHCl$_3$); IR (CHCl$_3$ smear) ν$_{max}$ 2935, 1738, 1480, 1280, 1150 cm$^{-1}$; $^1$H NMR (500 MHz, CDCl$_3$) δ 5.67–5.62 (m, 1H, C=C—H), 5.40–5.35 (m, 2H, H-4, C=C—H), 5.22 (dd, 1H, J=7.9, 10.4 Hz, H-2), 5.08 (dd, 1H, J=3.3, 10.5 Hz, H-3), 4.51 (d, 1H, J=7.9 Hz, H-1), 4.12–4.17 (m, 2H, H-6 and H-6'), 4.01 (dd, 1H, J=7.1, 11.0 Hz, H-a), 3.94 (t, 1H, J=6.8Hz, H-a'), 3.84 (dd, 1 H, J=6.1, 10.4 Hz, CH—OSi), 3.53 (dd, 1H, J=4.4, 10.3Hz, H-5), 3.45 (dd, 1 H, J=5.6, 10.4Hz, CH—N$_3$), 1.99–2.03 (m, 2H, C=C—CH$_2$), 1.32–1.10 (m, 48H, CH$_2$ and COC(CH$_3$)$_3$), 0.88–0.84 (m, 12H, CH$_3$ and SiC(CH$_3$)$_3$), 0.01 and 0.06 (singlets, 3H each, Si(CH$_3$)$_2$).

This product (1.66 grams) in 11.8 milliliters benzene was treated with 0.93 grams triphenylphosphine and 0.32 milliliters water. Flash chromatography was performed with 45% ethyl acetate in petroleum ether to yield a compound having structure XIV where R$_p$ has structure X and R$_6$ is Si(C(CH$_3$)$_3$)(CH$_3$)$_2$. Rf=0.60 (5% methanol in CH$_2$Cl$_2$); $[\alpha]_D^{24}$=−6.5° (c=0.54, CHCl$_3$); IR (CHCl$_3$ smear) ν$_{max}$ 2935, 1740, 1735, 1480, 1280, 1150 cm$^{-1}$; $^1$H NMR (500 MHz, CDCl$_3$) 5.63–5.57 (m, 1H, C=C—H), 5.38 (d, 1H, J=3.2 Hz, H-4), 5.31 (dd, 1H, J=7.6, 5.4 Hz, C=C—H), 5.20 (dd, 1H, J=7.8, 10.5 Hz, H-2), 5.08 (dd, 1H, J=3.3, 10.4 Hz, H-3), 4.48 (d, 1H, J=7.8 Hz, H-1), 4.12 (dd, 1H, J=6.6, 11.0Hz, H-a), 4.01 (dd, 1H, J=7.0, 11.0 Hz, H-a'), 3.94–3.91 (m, 2H, H-6 and H-6'), 3.87 (dd, 1H, J=6.3, 9.3 Hz, CH—OSi), 3.54 (dd, 1H, J=3.6, 10.3 Hz, H-5), 2.76–2.72 (m, 1H, CH—NH$_2$), 2.03–1.99 (m, 2H, C=C—CH$_2$) 1.41–1.07 (m, 48H, CH$_2$ and COC(CH$_3$)$_3$), 0.86 (t, 3H, CH$_3$), 0.85 (s, 9H, SiC(CH$_3$)$_3$), 0.04 and −0.01 (singlets, 3H each, Si(CH$_3$)$_2$).

This compound (1.32 grams) in 14.5 milliliters methylene chloride was then treated with 9 milligrams dimethylaminopyridine, 303 microliters triethylamine, and 540 microliters stearoyl chloride. Flash chromatography was performed with 15% ethyl acetate in petroleum ether to give a compound having structure XIV where R$_p$ has structure X and R$_6$ is Si(C(CH$_3$)$_3$)(CH$_3$)$_2$. Rf=0.36 (15% ethyl acetate in petroleum ether); $[\alpha]_D^{22}$=−7.2° (c=0.64, CHCl$_3$); IR (CHCl$_3$ smear) ν$_{max}$ 2935, 1735, 1670, 1480, 1280, 1150 cm$^{-1}$; $^1$H NMR (500 MHz, CDCl$_3$) δ 5.63–5.54 (m, 1H, C=C—H), 5.46 (d, 1H, J=8.8, NH), 5.38 (d, 1H, J=3.3 Hz, H-4), 5.35 (dd, 1H, J=7.6, 15.4 Hz, C=C—H), 5.16 (dd, 1H, J=7.7, 10.4 Hz, H-2), 5.09 (dd, 1H, J=3.3, 10.4 Hz, H-3), 4.48 (d, 1H, J=7.7 Hz, H-1), 4.16–4.09 (m, 3H, H-6,H-6' and CH—N), 4.03–3.92 (m, 3H, H-a, H-a' and CH—OSi), 3.44 (dd, 1H, J=3.7, 9.4 Hz, H-5), 2.14–1.95 (m, 4H, C=C—CH$_2$ and COCH$_2$), 1.35–1.02 (m, 78 H, CH$_2$ and COC(CH$_3$)$_3$), 0.86 (t, 6H, CH$_3$), 0.85 (s, 9H, SiC(CH$_3$)$_3$), 0.04 and −0.01 (singlets, 3H each, Si(CH$_3$)$_2$).

This compound (1.61 grams) in 9 milliliters tetrahydrofuran was treated with 1.5 milliliters of a 1.0 molar solution of tetrabutyl ammonium fluoride in tetrahydrofuran and flash chromatography was performed with 30% ethyl acetate in petroleum ether to yield a compound having structure I where R$_c$ is R$_p$ and has structure X, n is 16 and x is 18. Rf=0.29 (30% ethyl acetate in petroleum ether); $[\alpha]_D^{22}$=−4.9° (c=0.70, CHCl$_3$); IR (CHCl$_3$ smear) ν$_{max}$ 2935, 1735, 1660, 1480, 1280, 1145 cm$^{-1}$; $^1$H NMR (500 MHz, CDCl$_3$) δ 6.02 (d, 1H, J=7.4 Hz, NH), 5.74–5.70 (m, 1H, C=C—H), 5.48 (dd, 1H, J=6.5, 15.4 Hz, C=C—H), 5.41 (d, 1H, J=3.0 Hz, H-4), 5.18 (dd, 1H, J=7.7, 10.5 Hz, H-2), 5.12 (dd, 1H, J=3.2, 10.5 Hz, H-3), 4.49 (d, 1H, J=7.7 Hz, H-1), 4.14 (dd, 1H, J=6.9, 11.1 Hz, H-6), 4.12–4.09 (m, 1H, CH=N), 4.07–4.01 (m, 3H, H-6', H-a and CH—OH), 3.97 (t, 1H, J=6.8 Hz, H-a'), 3.67 (dd, 1H, J=2.6, 7.6 Hz, H-5), 3.20 (d, 1H, J=7.9 Hz, OH), 2.15 (t, 2H, J=7.7 Hz, COCH$_2$), 2.03 (dd, 2H, J=7.0, 14.3 Hz, C=C—CH$_2$), 1.62 (m 2H COCH$_2$CH$_2$) 1.38–1.09 (m 76H CH$_2$ and COC(CH$_3$)$_3$), 0.88 (t, 6H, J=6.9, CH$_3$).

This compound (1.35 grams) in 25 milliliters methanol was treated with 25 milligrams sodium methoxide and 0.50 grams amberlist resin and flash chromatography with 15% methanol in methylene chloride afforded the galactosyl ceramide having structure I where $R_c$ is galactose, n is 16 and x is 18. Rf=0.36 (15% methanol in $CH_2Cl_2$); $[\alpha]_D^{22}=-0.20°$ (c=1.0, 50% methanol in chloroform); $^1$H NMR (500 MHz, $CD_3OD$:$CDCl_3$=3:2) δ 5.70 (dt, 1H, J=6.8, 15.2 Hz, C=C—H), 5.46 (dd, 1H, J=7.8, 15.2 Hz, C=C—H), 4.23 (d, 1H, J=7.6 Hz, H-1), 4.19 (dd, J=4.5, 10.1 Hz, H-a), 4.11 (t, 1H, J=7.8 Hz, (HO)CH—C=C), 4.00–3.97 (m, 1H, CH—N), 3.86 (d, H, J=3.3 Hz, H-4), 3.80 (dd, 1H, J=6.8, 11.4 Hz, H-6), 3.74 (dd H, J=5.1, 11.4 Hz, H-6'), 3.60 (dd, 1H, J=3.2, 10.1 Hz, H-a'), 3.56 (dd, 1H, J=7.6, 9.6 Hz, H-2), 3.53–3.48 (m, 2H, H-3 and H-5), 2.18 (t, 2H, Hz, $COCH_2$), 2.03 (dt, 1H, J=6.8, 7.2 Hz, C=C—$CH_2$), 1.28 (m, 52H, $CH_2$), 0.89 (t, 6H, J=6.9 Hz, $CH_3$).

EXAMPLE 3

PREPARATION OF GLOBOTRIAOSYLCERAMINE

The method in Example 1, Section B was followed, except that 660 milligrams sphingosine equivalent in 1.5 milliliters methylene chloride and 179 milligrams glycosyl donor $R_pF$, where $R_p$ has structure XII, in 1.5 milliliters methylene chloride were added to a flask containing 62 milligrams $AgClO_4$, 57 milligrams $SnCl_2$, 300 milligrams 4 Angstrom molecular sieves and 17 microliters of 2,6-lutidine in 1.5 milliliters methylene chloride. Flash chromatography with 22% ethyl acetate in petroleum ether furnished, as a white foam, a compound having structure VIII where $R_p$ has structure XI and $R_6$ is $Si(C(CH_3)_3)(CH_3)_2$ Rf=0.45 (silica, 30% EtOAc in petroleum ether); $[\alpha]_D^{23}=+27.5°$ (c=1.6, $CHCl_3$); IR ($CHCl_3$ smear) $\nu_{max}$ 2980 (m), 2940 (m, 2865 (m), 2110 (m), 1750 (s), 1485 (m) cm$^{-1}$; $^1$H NMR (500 MHz, $CDCl_3$) δ 8.06–7.49 (m, 5H, aromatic), 5.61 (dt, J=15.4, 7.7 Hz, 1H, C=C—H), 5.41 (d, J=2.3 Hz, 1H, H-4''), 5.34 (dd, J=15.4, 7.3 Hz, 1H, C=C—H), 5.27 (dd, J=10.9, 3.3 Hz, 1H, H-3''), 5.20 (dd, J=9.6 Hz, 1H, H-3), 5.14 (dd, J=10.8, 3.5 Hz, 1H, H-2''), 5.12 (dd, J=10.3, 7.9 Hz, 1H, H-2') 5.01 (d, J=3.4 Hz, 1Hz, H-1''), 4.89 (dd, J=10.1, 2.5 Hz, 1H, H-3'), 4.88 (dd, J=9.4, 7.9 Hz, 1H, H-2), 4.78 (dd, J=11.9, 3.1 Hz, 1H, H-6a''), 4.53 (dd, J=11.7, 1.5 Hz, 1H, H-6a'), 4.49–4.46 (m, 3H, H-1, H-1', H-6a), 4.42 (dd, J=7.0, 7.3 Hz, 1H, CH—O), 4.24 (dd, J=10.8, 7.9 Hz, 1H, CH—O), 4.14–4.06 (m, 3H, CH—O), 4.02 (d, J=1.8 Hz, 1H, H-4'), 3.95 (dd, J=9.6 Hz, 1H, H-4), 3.85 (m, 1H, CH—O), 3.73 (dd, J=10.4, 6.9 Hz, 1H, CH—O), 3.51–3.48 (m, 2H, CH—O), 3.39 (m, 1H, CH—$N_3$), 2.11, 2.10, 2.05, 1.95 (singlets, 3H each, acetates), 1.98 (dt, J=7.6, 6.5 Hz, 2H, C=$CH_2$), 1.34–1.03 (m, 67H, $CH_2$ and pivalates), 0.87–0.82 (m, 12-H, $SiC(CH_3)_3$ and $CH_3$), 0.02 and 0 01 (singlets, 3H each, Si-$CH_3$).

This compound (161 milligrams) in 1 milliliter benzene was treated with 52 milligrams triphenylphosphine and 38 microliters of water. Flash chromatography was performed with 5% methanol in methylene chloride to yield a compound having structure XIV where $R_p$ has structure XI and $R_6$ is $Si(C(CH_3)_3)(CH_3)_2$.

This compound (144 milligrams) in 0.9 milliliters methylene chloride was treated with 1.0 milligram dimethylaminopyridine, 25 microliters triethylamine, and 51 microliters stearoyl chloride and gave a compound having structure XIV, where $R_p$ has structure XI and $R_6$ is $Si(C(CH_3)_3)(CH_3)_2$, as a white foam after flash chromatography with 25% ethyl acetate in petroleum ether. Rf=0.40 (silica, 30% EtOAc in petroleum ether); $[\alpha]_D^{23}=+27.8°$ (c=0.4, $CHCl_3$); IR ($CCl_4$ smear) $\nu_{max}$ 3460 (w), 2980 (s), 2940 (s), 2870 (s), 1750 (s), 1690 (m), 1490 (s), 1285 (s) cm$^{-1}$; $^1$H NMR (500 MHz, $CDCl_3$) δ 8.06–7.49 (m, 5H, aromatic), 5.45 (dt, J=15.4, 7.6 Hz, 1H, C=C—H), 5.43-5.38 (m, 2H, NH, C-4''), 5.32 (dd, J=15.3, 7.5 Hz, 1H, C=C—H), 5.28 (dd, J=10.3 Hz, 1H, H-3''), 5.20 (dd, J-9.5 Hz, 1H, H-3), 5.15–5.10 (m, 2H, H-2' H-2''), 5.02 (d, J=3.1 Hz 1H, H-1''), 4.90–4.84 (m, 2-H, H-2,H-3'), 4.77 (dd, J=11.4, 3.0 Hz, 1H, H-6a''), 4.51–4.41 (m, 5H, H-1, H-1' and 3 CH—O), 4.23 (dd, J-10.2, 9.5 Hz, 1H, CH—O), 4.18–4.07 (m, 3H, CH—O), 4.04–4.01 (m, 2H CH—O), 3.96–3.93 (m, 2H, CH—N and CH—O), 3.85 (m, J=5.7 Hz, 1H, CH —O), 3.48 (m, J=8.3 Hz, 1H, CH—O), 3.43 (m, J=6.9 Hz, 1H, CH—O), 2.11, 2.09, 2.05, 1.95 (singlets, 3H each acetates), 2.01 (m, 4H, C(O)$CH_2$, C=C—$CH_2$), 1.52 (m, 2H C(O)$C_2$—$CH_2$), 1.26–1.04 (m, 95H, $CH_2$ and pivalates), 0.86 (t, 6.5 Hz, 6H, $CH_3$, 0.81 (singlets, 9H, $SiC(CH_3)_3$), −0.41 and −0.51 (singlets, 3H each, $Si(CH_3)_2$).

This compound (77 milligrams) in 0.4 milliliters tetrahydrofuran was treated with 44 microliters of a 1 molar solution of tetrabutylammonium fluoride in tetrahydrofuran. Flash chromatography with 30% ethyl acetate in petroleum ether gave a compound having structure I where $R_c$ is $R_p$ and has structure XI, n is 16 and x is 18.

This compound (60 milligrams) in 0.7 milliliters methanol was treated with 2 milligrams sodium methoxide and, after the reaction was complete, 30 milligrams Amberlite-15 resin. Flash chromatography with 60:25:4 $CHCl_3$:methanol:water yielded $Gb_3$ (structure VII) as a white solid. Rf=0.35 (silica, 60:25:4, chloroform:methanol:water); $[\alpha]_D^{23}$ +24.1° (c=0.44, pyridine); $^1$H NMR (500 MHz, 49:1, DMSO-$d_6$:$D_2O$) δ 5.53 (dt, J=15.3, 7.7, 1H, C=C—H), 5.33 (dd, J=15.4, 7.1 Hz, 1H, C=C—H), 4.78 (d, J=3.7 Hz, 1H, H-1''), 4.25 (d, J=7.6 Hz, 1H, H-1'), 4.15 (d, J=7.8 Hz, 1H, H-1), 4.05 (t, J=6.1 Hz, 1H, H-5''), 3.93 (dd, J-10.2, 5.0 Hz, 1H, H-1 cer), 3.88 (t, J-7.5 Hz, 1H, H-3 cer), 3.80–3.28 (m, 18H, CH—O and DHO peak), 3.04 (t, J=8.0 Hz 1H, H-2), 2.01 (t, J=7.4 Hz, 1H, C=C—$CH_2$), 1.91 (m, 2H, $COCH_2$), 1.43 (m, 2H, $COCH_2$—$CH_2$), 1.31–1.11 (m, 50H, $CH_2$), 0.83 (t, J=6.8 Hz, 6 H, $CH_3$); $^{13}$C NMR (125 MHz, DMSO-$d_6$) δ 171.7, 131.5, 131.3, 103.8, 103.5, 100.6, 80.7, 77.1, 75.0, 74.8, 74.4, 73.2, 72.8, 71.1, 70.8, 70.7, 69.2, 68.8, 68.6, 60.4, 59.3, 52.9, 39.0, 35.6, 31.8, 29.2, 29.1, 28.8, 28.7, 25.4, 22.2, 13.8.

Those skilled in the art will appreciate that numerous changes and modifications may be made to preferred embodiments of the invention and that such changes and modifications may be made without departing from the spirit of the invention. It is therefore intended that the appended claims cover all such equivalent variations as fall within the true spirit and scope of the invention.

What is claimed is:
1. A compound having the formula:

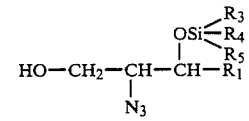

wherein $R_1$ is alkenyl having from about 4 to about 28 carbon atoms, and $R_3$, $R_4$, and $R_5$ are the same or different and are hydrocarbyl having from about 1 to about 7 carbon atoms.

2. The compound of claim 1 wherein $R_1$ is dodecenyl.

3. The compound of claim 1 wherein $R_3$ and $R_4$ are methyl and $R_5$ is tertiary butyl.

4. The compound of claim 1 comprising at least about 95% of a single stereochemical form.

5. The compound of claim 1 comprising at least about 95% D-erythro enantiomer.

6. The compound of claim 1 comprising at least about 95% D-erythro enantiomer, wherein $R_1$ is dodecenyl, $R_3$ and $R_4$ are methyl, and $R_5$ is tertiary butyl.

7. The compound of claim 1 wherein $R_1$ is pentadecenyl.

8. The compound of claim 1 comprising at least about 95% D-erythro enantiomer, wherein $R_1$ is pentadecenyl, $R_3$ and $R_4$ are methyl, and $R_5$ is tertiary butyl.

* * * * *